(12) United States Patent
Hansen et al.

(10) Patent No.: US 8,353,884 B2
(45) Date of Patent: Jan. 15, 2013

(54) ANAL PATCH

(75) Inventors: Michael Hansen, Gilleleje (DK); Peter Kragh, Tikoeb (DK); Claus Bo Voege Christensen, Snekkersten (DK)

(73) Assignee: Coloplast A/S, Humlebaek (DK)

( * ) Notice: Subject to any disclaimer, the term of this patent is extended or adjusted under 35 U.S.C. 154(b) by 612 days.

(21) Appl. No.: 12/227,219

(22) PCT Filed: May 10, 2007

(86) PCT No.: PCT/DK2007/000223
§ 371 (c)(1),
(2), (4) Date: Nov. 12, 2008

(87) PCT Pub. No.: WO2007/134600
PCT Pub. Date: Nov. 29, 2007

(65) Prior Publication Data
US 2009/0093784 A1  Apr. 9, 2009

(30) Foreign Application Priority Data
May 19, 2006  (DK) .................................. 2006 00694

(51) Int. Cl.
*A61F 13/02* (2006.01)
*A61F 13/00* (2006.01)

(52) U.S. Cl. ........................ 604/307; 604/304; 604/358

(58) Field of Classification Search ............ 604/59–360, 604/385.01, 385.101, 367, 375, 378
See application file for complete search history.

(56) References Cited

U.S. PATENT DOCUMENTS

| | | | |
|---|---|---|---|
| 4,212,296 A * | 7/1980 | Schaar | 602/42 |
| 5,695,484 A | 12/1997 | Cox | |
| 6,059,763 A * | 5/2000 | Brown | 604/385.17 |
| 6,313,371 B1 * | 11/2001 | Conant et al. | 604/359 |
| 6,406,464 B1 | 6/2002 | Palumbo et al. | |
| 6,733,482 B1 * | 5/2004 | Coles et al. | 604/355 |
| 6,913,573 B1 * | 7/2005 | Viscomi et al. | 600/29 |
| 2005/0182376 A1 | 8/2005 | Fleming | |

FOREIGN PATENT DOCUMENTS

| | | |
|---|---|---|
| WO | WO 01/85073 A1 | 11/2001 |
| WO | WO 2004/010911 A1 | 2/2004 |
| WO | WO 2006/005717 A2 | 1/2006 |

* cited by examiner

*Primary Examiner* — Michele M Kidwell
(74) *Attorney, Agent, or Firm* — Coloplast Corp., Coloplast A/S; Daniel G. Chapik; Nicholas R. Baumann

(57) ABSTRACT

An anal patch comprising an absorbent pad (3) in a shape with two substantially parallel flat surfaces and a contact surface perpendicular to the flat surfaces, the area of the contact surface being smaller than each of the two parallel flat surfaces, an adhesive part, comprising an adhesive coated backing layer (4), having a central aperture (8) wherein at least a part of the contact surface of the absorbent pad is aligned with the aperture of the adhesive part.

13 Claims, 3 Drawing Sheets

ANAL PATCH

This is a national stage of PCT/DK2007/000223 filed May 10, 2007 and published in English, which has a priority of Denmark No. PA2006 00694 filed May 19, 2006, hereby incorporated by reference.

BACKGROUND OF THE INVENTION

1. Field of the Invention

The invention relates to an anal patch for handling low level incontinence and soiling from the anal area.

Following colorectal cancer treatment, after giving birth or due to otherwise induced or occurring partial loss of sphincter control, a fecal incontinent situation can arise requiring management.

The key users of the invention would thus usually be more senior people (and women from after giving birth) of both sexes, typically plus 60 years of age. Low level fecal incontinence is today not adequately addressed in terms of specific devices to help the patient, and mostly homemade solutions are used, like e.g. female hygienic pads are used, cotton pads or toilet tissue.

2. Description of the Related Art

Different non-invasive solutions that can be placed in the perianal area, specifically the perineum and sacral area of the body in order to collect fecal material or soiling output are known in the art. A number of products/solutions have been described in the patent literature, but few besides hygienic pads and alike are available in the market.

From International patent application Ser. No. WO 06/005717 is known a container for collecting excretions, draining collections, purging ostomies or the like. The container comprises an adhesive patch for applying to the perianal area and a tool for application of this in the form of two blades between which spring means are interposed. The adhesive patch is with radial slits.

US patent application Ser. No. US 2005/0182376 A1 discloses an anal hygienic pad in the form of a wedge-shaped absorbent pad for squeezing in between buttocks without the use of adhesive. The system is unreliable as the pad is not secured to the body and may thus displace when the user moves, as well as the pad is rather thick and may cause discomfort.

U.S. Pat. No. 5,695,484 A discloses an anal patch for fecal incontinence. The patch is in the form of an adhesive patch with an absorbent layer, similar to a wound dressing. The patch has the shape of a saddle in order to provide better fit to the perianal area. The patch may be difficult to apply correctly and without contaminating the users hand, as well as stress may be built up in the patch while the user moves and cause discomfort and/or leakage.

Thus there is still a need for an anal patch or dressing being easy to apply, comfortable and with good adhesiveness and safety when moving around. The anal patch of the present invention fulfills these and other objects.

SUMMARY OF THE INVENTION

One object of the present invention is to provide an anal patch that is easy and non-soiling to apply.

Another object of the invention is to provide an anal patch that is comfortable for the user to wear, optionally being unnoticeable in use.

Yet another object is to provide a patch that is safe in operation, flexible and adaptable to anatomical configuration of different users, and that reduces the risk of leakage. The patch should be conformable to the perianal area and mouldable to the skin.

Yet another object is to provide a patch that with a good initial tack of adhesive is able to adhere to hairy skin, skin folds and around haemorrhoids. The patch should be easy to remove without unacceptable levels of pain.

Still another object of the invention is to provide an anal patch that is capable of flatulence odour neutralization and/or flatus sound silencing.

BRIEF DESCRIPTION OF THE DRAWINGS

The invention is disclosed more in detail with reference to the drawings in which.

DETAILED DESCRIPTION OF THE PRESENT INVENTION

Figure 1:
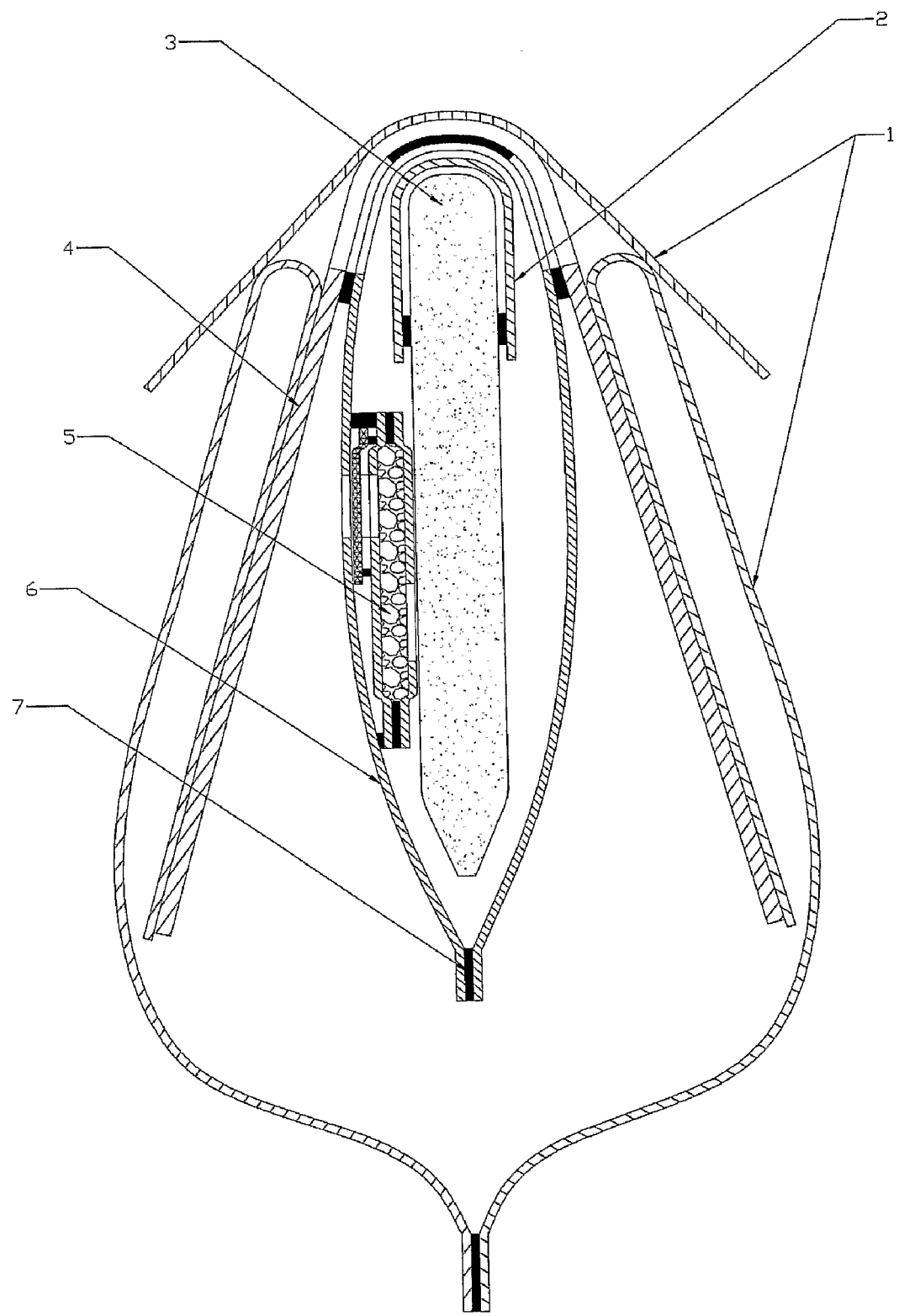
FIG. 1 shows an embodiment of the invention in cross-section.

The invention relates to an anal patch comprising an absorbent pad in a shape with two substantially parallel flat surfaces and a contact surface perpendicular to the flat surfaces, the area of the contact surface being smaller than each of the two parallel flat surfaces, an adhesive part, comprising an adhesive and a backing layer, having an aperture in the center and wherein at least a part of the contact surface of the absorbent pad is aligned with the aperture of the adhesive part.

The absorbent pad is preferably in the form of a flat pad comprising absorbent material, having two main surfaces, and smaller surfaces defining an edge portion. The main surfaces are preferably substantially parallel, but may also be curved to define a pillow shape or the surfaces may diverge slightly from each other's to define a wedge shape. The overall impression of the shape of the absorbent pad is however a sheet having a thickness being smaller then the length or width of the pad.

The contact surface is preferably a linear or slightly curved surface, in order to follow the anatomy of the intergluteal area. The other surfaces of the pad, apart from the main flat surfaces, may also have any suitable shape, such as linear or curved. In a preferred embodiment of the invention the absorbent pad is in the shape of a flat half-circle, the contact surface being the straight edge portion. The size and shape of the absorbent pad may be dependent of the expected amount of effluent/wear time and a desire of a discrete appearance.

The absorbent pad is extending from the contact surface and away from the anal orifice.

Preferably the absorbent pad comprises an impermeable cover layer on all surfaces, except the part of the contact surface aligned with the aperture of the adhesive part, for reception of fecal or other output. The cover layer serves as a barrier layer by controlling any absorbed effluent from leaking from the patch. The cover layer may be any suitable film being capable of retaining water and odor. The cover layer may be attached to the absorbent material by lamination or adhesive, but preferably the material is wrapped in, but not directly attached to the cover layer. This facilitates a larger flexibility of the pad.

The absorbent pad may be provided with a net wrapping for controlling the absorbent material.

The adhesive part of the patch of the present invention is in the form of a backing layer comprising an adhesive on the skin-facing surface. The adhesive may be in he form of a continuous or discontinuous layer. The adhesive may be any skin-friendly adhesive suitable for the purpose. The skin around anal orifice is often humid and an adhesive capable of handling moisture environment without loosing tack is preferred. Furthermore, the area may be sensible, and sometimes also hairy, demanding an adhesive that is easy to remove without unreasonable pain. An especially suitable adhesive may be a silicone based adhesive, preferably coated in a pattern or perforated on the backing layer in order to allow breathability of the patch. Use of pattern-coated adhesive may also facilitate less adhesive surface and thus an easier release from release liner and/or skin.

The backing layer should be able to follow the movements of the skin and be comfortable for the user. Suitable material for such backing layer may be a polymer film or a non-woven material. The material should be compatible with the cover layer of the absorbent pad in order to facilitate welding or adhering these layers to each other.

The adhesive coated backing layer is attached to the absorbent pad in a manner so at least a part of the contact surface of the absorbent pad is aligned with the aperture of the adhesive part. This enables direct contact for the absorbent pad to the skin/anal orifice. The adhesive part and the absorbent pad may be attached to each other by known means, e.g. welding or adhesive.

Figure 4:
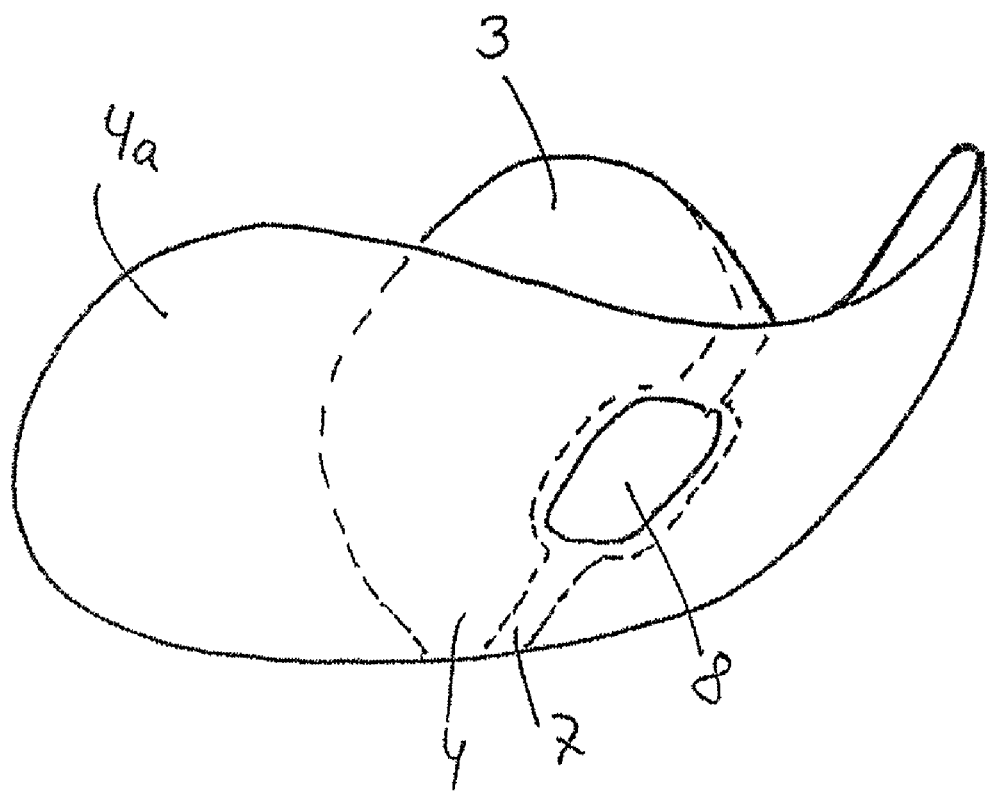

With specific reference to FIG. 4, preferably only a part of the backing layer 4 is fixed to the absorbent pad 3, for example at zone of the welding 7. The adhesive backing layer 4 may extend further than the zone (7) where it is attached to the pad 3 and into an adhesive flange 4a. The backing layer 4 is only attached to the absorbent pad 3 in the area 7 surrounding the aperture 8, thus providing that the non-attached part 4a (hereinafter called the flange 4a) is able to move independently of the absorbent pad 3 and the contact area 7. The adhesive part (the flange 4a) and the absorbent pad 3 are freely movable. The mobility of the patch is thereby greatly enhanced, compared to the anal dressings known in the art; these are often in the form of a backing layer with an absorbent pad attached to its main surface.

When the patient moves, the buttocks move and displace with respect to each others, creating torsion and stress in the dressing, the effect being enhanced by the often rather stiff and thick absorbent pad trying to follow the movements of the buttocks. In the patch of the present invention the absorbent pad is not directly attached to the buttocks, but only to the natal cleft surrounding the anal orifice via the contact surface, while rest of the backing layer, the flange, being thin and flexible, are attached to the skin, and may extend to the buttocks. Thus the stress build up in this patch during movement of the buttocks is considerably lower, facilitating a lower risk of undesired detachment or leakage as well as being more comfortable for the user. The absorbent pad will lie parallel but unattached to the adhesive flange when mounted on a user. The adhesive backing layer and the absorbent pad are only connected at the area around the contact surface and do thus allow free movement of the buttocks.

The flange may be large and extend to the buttock, or it may be smaller only covering the skin next to the anal orifice.

The aperture is preferably surrounded by adhesive layer for facilitating a snug fit to the skin around anal orifice thus reducing the risk of leakage. The contact surface is designed to fit in the intergluteal area, between the buttocks, specifically to the perineum and the sacral areas, in the natal cleft.

The cover layer surrounding the absorbent pad may in one embodiment of the invention comprise a filter. The filter facilitates outlet of gas and is optionally provided with odor controlling means. The gas filter allows filtration of flatulence for odour neutralization. The filter may e.g. be of the kind used for venting ostomy bags.

The aperture of the adhesive part may be central by being located on the contact surface, but it may be preferred that the aperture is dislocated on the contact surface, leaving a larger space for the sacral area and a smaller area for the perineum area. This embodiment is preferred due to the anatomy of the area.

The anatomy of man in the perianal area is very diverse. Also between sexes, the major difference is exposed in the distance from the anus to the vagina or Scrotum. Adult women have a very short distance of approximately 1,5-3 cm and men from 3-7 cm, increasing with age.

The patch may be removed by pulling the absorbent pad, then the adhesive may detach first at the contact surface, and then the rest of the adhesive backing layer may detach. The adhesive backing layer may fold along the contact surface during the detachment, bringing the adhesive surface to adhere to itself. Thus the patch will be "closed", the messy contact surface may be enclosed in the adhesive backing layer, providing a hygienic solution.

One or more release liners may protect the adhesive surface of the patch of the invention. Preferably, a first release liner covers the contact surface, while second release liners protect the rest of the adhesive surface.

Removing the first release liner covering the contact surface followed by positioning of the pad, so that the opening in the pad is facing the anal orifice and having the shortest adhesive part pointing towards the front of the person does the mounting of the anal pad. Inserting the pointing and middle finger on each side of the absorbent element, and pressing the pad against the natal cleft positions the pad. The adhesive may fix the anal pad to the natal cleft, and the second release liners are then removed to fix the pad firmly to the skin.

The length of the part adhering to the perineum is between preferably between 10-50 mm.

The aperture of adhesive backing layer may vary from 35 mm diameter to an oval of 35×60 mm.

The total length of the patch along the contact surface is preferably between 70 to 140 mm.

The anal patch of the present invention may be suitable for use for other indications like bleeding from fistulas, haemorrhoids, or medication from the anal patch.

The patch may be produced by different methods.

The invention also relates to a method preparing an anal patch comprising an absorbent pad in a shape with two substantially parallel flat surfaces and a contact surface perpendicular to the flat surfaces, the area of the contact surface being smaller than each of the two parallel flat surfaces, an adhesive part, comprising an adhesive and a backing layer, having an aperture in the center and wherein at least a part of the contact surface of the absorbent pad is aligned with the aperture of the adhesive part, the method comprising the steps of: Laminating a backing layer to an adhesive layer and die cut the laminate to final shape, welding a gas filter to a cover layer and welding the cover layer to the backing film, cutting a central aperture in the backing layer, cutting an absorbent material into a desired shape, folding the cover layer around the absorbent pad and welding the cover layer to enclose the absorbent material.

In one embodiment of the invention a net foil is welded to at least a part of the absorbent material.

The invention further relates to a method of application of an anal patch comprising the steps of: Providing an anal patch comprising an absorbent pad in a shape with two substantially parallel flat surfaces and a contact surface perpendicular to the flat surfaces, the area of the contact surface being smaller than each of the two parallel flat surfaces, an adhesive part, comprising an adhesive coated backing layer, having a central aperture and wherein at least a part of the contact surface of the absorbent pad is aligned with the aperture of the adhesive part, and a first release liner covering the contact surface, and second release liners covering the rest of the adhesive surface, removing the central release liner, inserting fingers on each side of the absorbent pad, bringing the contact surface of the patch into contact with the anal orifice, removing the second release liners, whereby the adhesive backing layer is brought in contact with the skin.

The patch may easily be applied with one hand, and the risk of getting messy fingers is low.

Description Of The Preferred Embodiments

The invention is now explained more in detail with reference to the drawings showing preferred embodiments of the invention.

In FIG. 1 is disclosed a preferred embodiment of the invention in cross-section. The anal patch comprises of an absorbent pad (3), comprising a wrapping of a cover layer (6) and provided with a gas filter (5). A net (2) is provided at the contact surface (9) of the absorbent pad (3). The net facilitates a pleasant non-stick surface against the anal orifice as well as it prevents flock from the absorbent material to escape. The adhesive backing layer (4) is having a central aperture (8) aligned with the contact surface of the absorbent pad (9) and extends from the aperture (8) and away from the absorbent pad (3) into a flange (4a). The adhesive layer is protected by a first release liner (1a) for covering the contact surface area, and second release liners (1b) for covering the adhesive surface of the flange. The second release liners (1b) may be folded at the contact surface end and extend backwards again, further than the backing layer (4a) and into a tab member (10). The tab members (10) of the wing release liners may be fixed to each others (10a), e.g. by welding or adhesive.

When applying the patch, the central release liner (1a) is removed, and fingers are inserted on each side of the absorbent pad (3) in the space between the flange (4a) and the pad (3). The contact surface (8) of the patch is brought in contact with the anal orifice and positioned, and then the tab member (10) of the second release liners (1b) are slowly pulled back, thus rolling the release liners (1b) off the adhesive surface (4a), concurrent with the inserted fingers presses the backing layer (4a) into contact with the skin. The application is easy and the risk of soiling the fingers is low.

Figure 2:
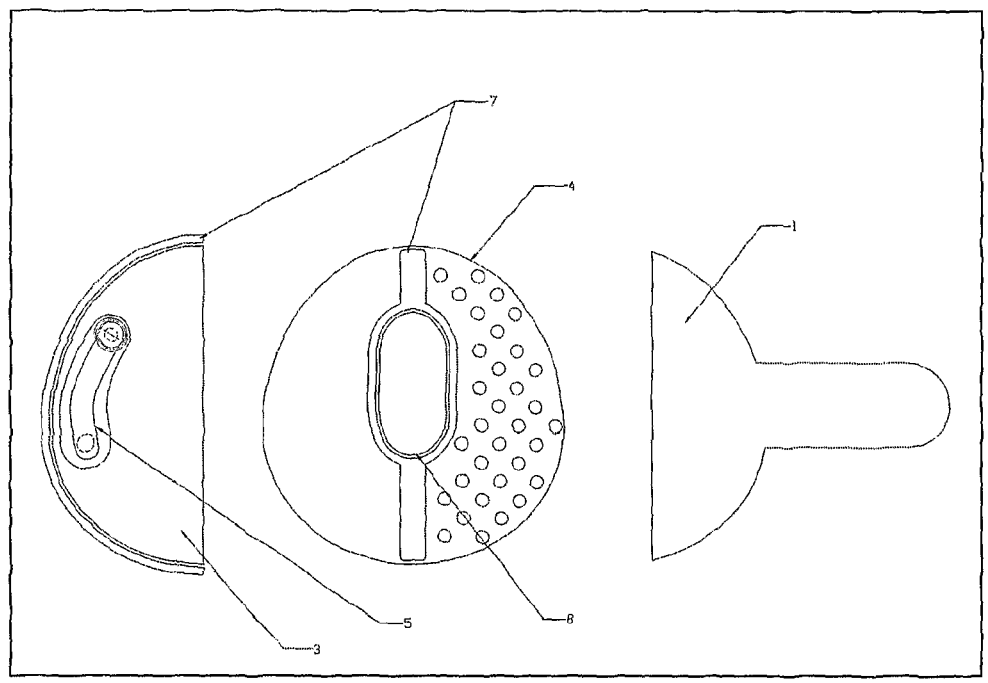
FIG. 2 shows the same embodiment in parts.

In FIG. 2 is disclosed the same embodiment of the invention in parts. The absorbent pad (3), in the form of a absorbent material having a shape of a half-circle, wrapped in a cover layer welded (7) along the curved edge and being provided with a gas filter (5). The backing layer (4) with a central aperture (8) and coated with a perforated layer of adhesive (indicated on the Figure by dots). The welding line (7) for attaching the absorbent pad to the backing layer is following the contact surface line and is surrounding the aperture (8). The backing layer of the adhesive part is welded to the absorbent pad only around the contact area. Finally, the second release liner (1b) is shown, with the tab member (10). The second release liner (1b) is shown folded along the line near the contact surface. If the flange is stretched by pulling, as may happen with movements of the intergluteal area, the welding between the cover layer of the absorbent pad and the adhesive part will become under pressure, thus altering the contact surface from a straight line and into a curved line. As the intergluteal area is slightly curved, the curved line will fit perfectly to the area even when exposed to heavy movements.

Figure 3:
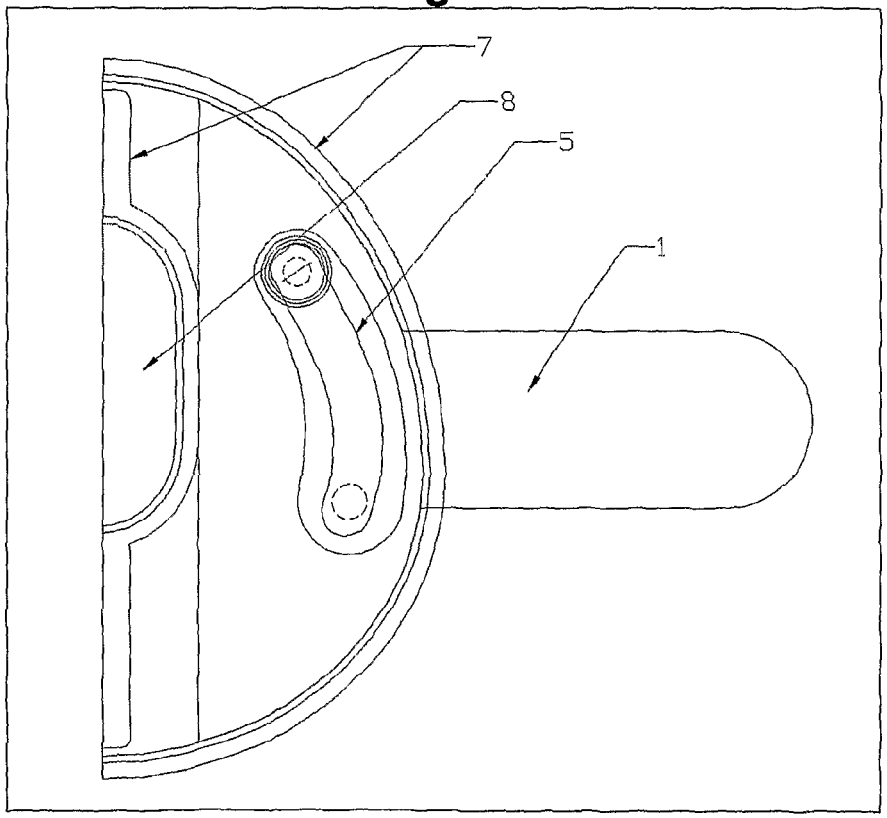
FIG. 3 shows a side view of the embodiment and FIG. 4 shows a perspective view of the embodiment.

FIG. 3 shows a "transparent" side view of the same embodiment.

FIG. 4 shows the embodiment in perspective, with the aperture (8) in the adhesive part (4) and the adhesive flange (4a) extending from the contact surface, indicated by the welding (7) around the aperture (8) and along the contact surface of the absorbent pad (3). The Figure shows the patch without release liners.

The invention claimed is:

1. An anal patch comprising:
   an absorbent pad provided with a contact surface; and
   an adhesive coated backing layer having a central aperture, the backing layer attached to the absorbent pad at an area around a peripheral edge of the central aperture with the contact surface of the absorbent pad placed over the aperture and exposed through the aperture of the backing layer;
   wherein the backing layer includes a flange that is unattached to the absorbent pad such that the flange is adapted to move independently of the absorbent pad;
   wherein the absorbent pad is oriented substantially perpendicular to the area at which the absorbent pad is attached to the backing layer.

2. The anal patch according to claim 1, wherein the absorbent pad comprises an impermeable cover layer on all surfaces, except on the contact surface of the absorbent pad that is aligned with the aperture of the adhesive coated backing layer.

3. The anal patch according to claim 1, wherein the absorbent pad is wedge shaped.

4. The anal patch according to claim 1, wherein main surfaces of the absorbent pad are curved.

5. The anal patch according to claim 1, wherein the absorbent pad extends from the contact surface and away from the central aperture.

6. The anal patch according to claim 1, wherein the aperture is surrounded by the adhesive coated backing layer.

7. The anal patch according to claim 1, wherein the absorbent pad comprises an effluent impermeable cover layer and a filter attached to the cover layer.

8. The anal patch according to claim 1, wherein the adhesive is covered by one or more release liners.

9. The anal patch according to claim 1, further comprising:
   a non-stick surface placed over the contact surface and within the central aperture.

10. The anal patch according to claim 9, wherein the non-stick surface is a net.

11. The anal patch according to claim 1, wherein the adhesive coated backing layer is only attached to the absorbent pad at the peripheral edge of the central aperture.

12. The anal patch according to claim 1, wherein the flange comprises a first flange extending away from one of two substantially parallel flat surfaces and a second flange extending away from an other of the two substantially parallel flat surfaces.

13. The anal patch according to claim 1, wherein the contact surface of the absorbent pad is adapted for contact with a surrounding area of an anal orifice of the user and the flange is adapted to move independently of the absorbent pad as the user moves.

* * * * *